(12) United States Patent
Eckert et al.

(10) Patent No.: US 8,535,370 B1
(45) Date of Patent: Sep. 17, 2013

(54) RADIOPAQUE MARKERS FOR ENDOVASCULAR GRAFT ALIGNMENT

(75) Inventors: Robin W. Eckert, San Jose, CA (US); Robert A. Vincent, Redwood City, CA (US)

(73) Assignee: Endovascular Technologies, Inc., Menlo Park, CA (US)

( * ) Notice: Subject to any disclaimer, the term of this patent is extended or adjusted under 35 U.S.C. 154(b) by 2339 days.

(21) Appl. No.: 10/349,588

(22) Filed: Jan. 23, 2003

(51) Int. Cl.
*A61F 2/06* (2013.01)

(52) U.S. Cl.
USPC .................. 623/1.34; 623/1.13; 623/1.35

(58) Field of Classification Search
USPC .............. 623/1.34–1.36, 1.13; 606/108, 194, 606/198
See application file for complete search history.

(56) References Cited

U.S. PATENT DOCUMENTS

| | | | |
|---|---|---|---|
| 3,657,744 A | 4/1972 | Ersek | |
| 4,061,134 A | 12/1977 | Samuels et al. | |
| 4,108,161 A | 8/1978 | Samuels et al. | |
| 4,140,126 A | 2/1979 | Choudhury | |
| 4,214,587 A | 7/1980 | Sakura, Jr. | |
| 4,577,631 A | 3/1986 | Kreamer | |
| 4,617,932 A | 10/1986 | Kornberg | |
| 4,728,328 A | 3/1988 | Hughes et al. | |
| 4,732,152 A | 3/1988 | Wallsten et al. | |
| 4,739,762 A | 4/1988 | Palmaz | |
| 4,787,899 A | 11/1988 | Lazarus | |
| 4,793,348 A | 12/1988 | Palmaz | |
| 4,795,458 A | 1/1989 | Regan | |
| 4,830,003 A | 5/1989 | Wolff et al. | |
| 4,899,732 A | 2/1990 | Cohen | |
| 4,969,896 A | 11/1990 | Shors | |
| 5,026,377 A | 6/1991 | Burton et al. | |
| 5,047,050 A | 9/1991 | Ardesani | |
| 5,064,435 A | 11/1991 | Porter | |
| 5,078,726 A | 1/1992 | Kreamer | |
| 5,104,399 A | 4/1992 | Lazarus | |
| 5,122,154 A | 6/1992 | Rhodes | |
| 5,123,917 A | 6/1992 | Lee | |
| 5,192,297 A | 3/1993 | Hull | |
| 5,201,757 A | 4/1993 | Heyn et al. | |

(Continued)

FOREIGN PATENT DOCUMENTS

| | | |
|---|---|---|
| DE | 9319267 | 4/1994 |
| EP | 0 461 791 A1 | 12/1991 |

(Continued)

OTHER PUBLICATIONS

Chuter, et al., "Transfemoral Endovascular Aortic Graft Placement," Journal of Vascular Surgery, vol. 18, No. 2, Aug. 1993, pp. 185-197.

(Continued)

*Primary Examiner* — Elizabeth Houston
(74) *Attorney, Agent, or Firm* — Brooks, Cameron & Huebsch, PLLC

(57) ABSTRACT

An endovascular prosthesis containing radiopaque markers for identifying the position of the prosthesis and for detecting any twisting of the prosthesis inside a corporeal vessel. The prosthesis may be a graft having a graft body with a wall defining a lumen. A plurality of radiopaque markers are disposed on the wall of the graft, with each individual marker appearing identical under fluoroscopy regardless of the grafts orientation inside the corporeal vessel, but the relative positions of individual markers relative to each other in a set indicate the prosthesis position and orientation.

5 Claims, 10 Drawing Sheets

(56) References Cited

U.S. PATENT DOCUMENTS

| | | | |
|---|---|---|---|
| 5,219,355 A | 6/1993 | Parodi et al. | |
| 5,275,622 A | 1/1994 | Lazarus et al. | |
| 5,316,023 A | 5/1994 | Palmaz et al. | |
| 5,360,443 A | 11/1994 | Barone et al. | |
| 5,387,235 A | 2/1995 | Chuter | |
| 5,395,334 A | 3/1995 | Keith et al. | |
| 5,397,345 A | 3/1995 | Lazarus | |
| 5,489,295 A | 2/1996 | Piplani et al. | |
| 5,562,724 A | 10/1996 | Vorwerk et al. | |
| 5,575,817 A | 11/1996 | Martin | |
| 5,628,788 A | 5/1997 | Pinchuk | |
| 5,632,772 A | 5/1997 | Alcime et al. | |
| 5,639,278 A | 6/1997 | Dereume et al. | |
| 5,653,743 A | 8/1997 | Martin | |
| 5,676,696 A | 10/1997 | Marcade | |
| 5,683,449 A | 11/1997 | Marcade | |
| 5,683,450 A | 11/1997 | Goicoechea et al. | |
| 5,716,365 A | 2/1998 | Goicoechea et al. | |
| 5,718,724 A | 2/1998 | Goicoechea et al. | |
| 5,723,004 A | 3/1998 | Dereume et al. | |
| 5,741,325 A | 4/1998 | Chaikof et al. | |
| 5,755,769 A | 5/1998 | Richard et al. | |
| 5,769,885 A * | 6/1998 | Quiachon et al. | 128/898 |
| 5,776,180 A | 7/1998 | Goicoechea et al. | |
| 5,800,508 A | 9/1998 | Goicoechea et al. | |
| 5,824,037 A | 10/1998 | Fogarty et al. | |
| 5,824,042 A | 10/1998 | Lombardi et al. | |
| 5,855,598 A | 1/1999 | Pinchuk | |
| 5,916,263 A | 6/1999 | Goicoechea et al. | |
| 5,938,696 A | 8/1999 | Goicoechea et al. | |
| 5,993,481 A | 11/1999 | Marcade et al. | |
| 6,015,431 A | 1/2000 | Thornton et al. | |
| 6,051,020 A | 4/2000 | Goicoechea et al. | |
| 6,099,558 A | 8/2000 | White et al. | |
| 6,102,938 A | 8/2000 | Evans et al. | |
| 6,117,167 A | 9/2000 | Goicoechea et al. | |
| 6,123,722 A | 9/2000 | Fogarty et al. | |
| 6,149,682 A | 11/2000 | Frid | |
| 6,165,213 A | 12/2000 | Goicoechea et al. | |
| 6,203,568 B1 | 3/2001 | Lombardi et al. | |
| 6,210,434 B1 * | 4/2001 | Quiachon et al. | 623/1.23 |
| 6,214,038 B1 * | 4/2001 | Piplani et al. | 623/1.11 |
| 6,221,102 B1 * | 4/2001 | Baker et al. | 623/1.36 |
| 6,660,033 B1 * | 12/2003 | Marcade et al. | 623/1.16 |
| 6,808,534 B1 * | 10/2004 | Escano | 623/1.23 |

FOREIGN PATENT DOCUMENTS

| | | |
|---|---|---|
| EP | 0 508 473 A2 | 10/1992 |
| EP | 0 539 237 A1 | 4/1993 |
| EP | 0 637 454 A1 | 2/1995 |
| EP | 0 646 365 A1 | 4/1995 |
| FR | 2 678 508 | 1/1993 |
| FR | 2 748 197 | 11/1997 |
| RU | 1217402 | 3/1986 |
| RU | 1318235 A1 | 6/1987 |
| RU | 1389778 A2 | 4/1988 |
| RU | 1457921 A1 | 2/1989 |
| RU | 1482714 A2 | 5/1989 |
| WO | 84/02266 | 6/1984 |
| WO | WO 95/01761 | 1/1995 |
| WO | WO 95/16406 | 6/1995 |

OTHER PUBLICATIONS

Parodi et al., "Transfemoral Intraluminal, Graft Implantation for Abdominal Aortic Aneurysms," Annals of Vascular Surgery, vol. 5, No. 6, 1991, p. 491-499.

Criado et al., "Transluminal Recanalization, Angioplasty and Stenting in Endovascular Surgery: Techniques and Applications," from Greenhalgh, Vascular and Endovascular Surgical Techniques, 3rd Editions, 1994, pp. 49-70.

Marin et al., "Endoluminal Surgical Graft Aorto—Bifemoral Reconstruction," from Greenhalgh, Vascular and Endovascular Sirgucal Techniques, 3 sup.rd Edition, 1994, pp. 100-104.

May et al., "Transluminal Placement of a Prosthetic Graft-Stent Device for Treatment of Subclavian Artery Aneurysm," Journal of Vascular Surgery, vol. 18, No. 6, Dec. 1993, pp. 1056-1059.

Clutter, T., "Bifurcated Endovascular Graft Insertion for Abdominal Aortic Aneurysm," from Greenhalgh, Vascular and Endovascular Surgical Techniques, 3 sup. rd Edition, 1994, pp. 92-99.

Moore, W.S., "Transfemoral Endovascular Repair of Abdominal Aortic Aneurysm Using the Endovascular Graft System Device," from Greenhalgh, Vascular and Surgical Techniques, 3 sup. rd Edition, 1994, pp. 78-91.

* cited by examiner

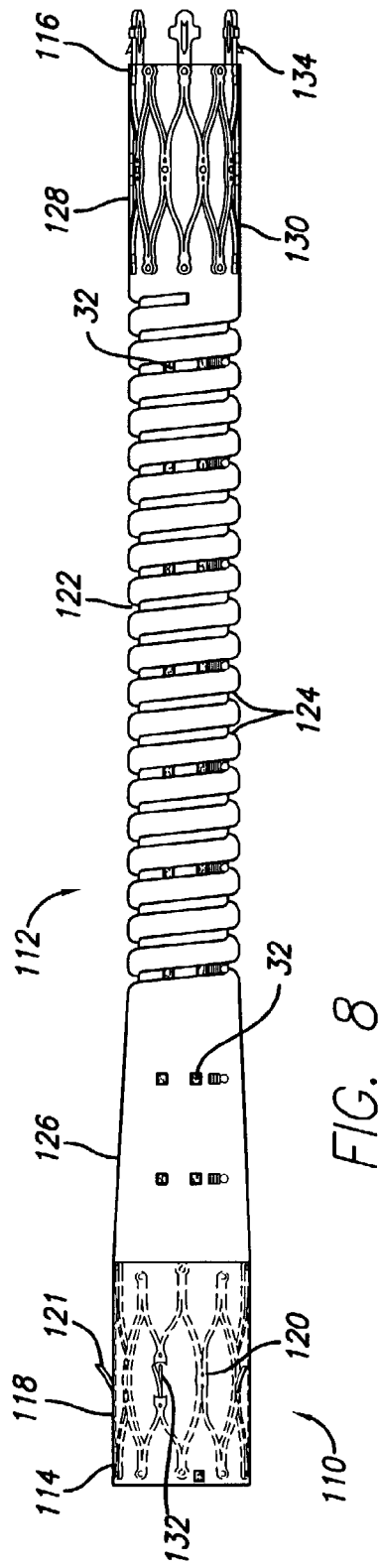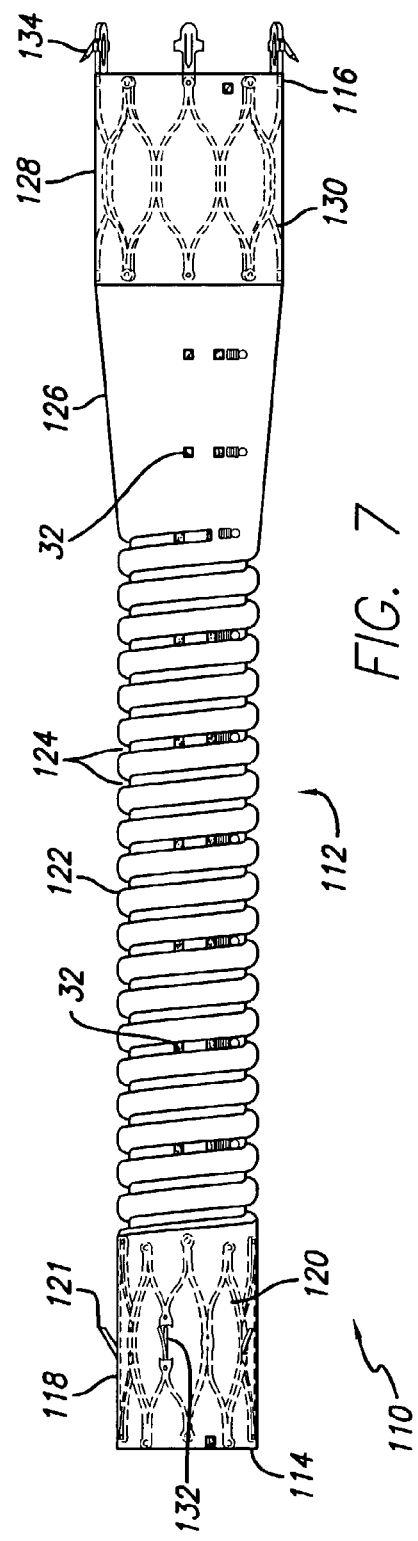
FIG. 8
FIG. 7

RADIOPAQUE MARKERS FOR ENDOVASCULAR GRAFT ALIGNMENT

FIELD OF THE INVENTION

The present invention is directed to the use of markers to determine the orientation of an object. Moreover, the present invention relates to the use of radiopaque markers on an endovascular product to determine the orientation and position of the endovascular product during an implantation procedure.

BACKGROUND OF THE INVENTION

It has been known within the art that a prosthesis can be used for intraluminal repair of a vessel, such as an abdominal aorta having an aneurysm. The prosthesis, which can be a graft and/or a stent, is positioned and secured in a vessel, with hooks or staples that are self expanding or mechanically extended by a user into the lumen of the vessel. The orientation and position of the prosthesis relative to the vessel is very important to the success of the operation, and therefore methods have been used to view the prosthesis under fluoroscopy.

Precise orientation and positioning of an endovascular prosthesis within a vessel is critical to the success rate of repairing aneurysms. Endovascular prostheses are typically introduced into the vascular system of a patient within a catheter following over a guide wire and into position at the repair site. The positioning of the catheter and prosthesis is typically monitored under fluoroscopy. Once in position, the prosthesis will be expanded from a contracted configuration to an expanded configuration to engage the vessel lumen. The prosthesis is usually anchored into healthy tissue above and below the aneurysm, allowing the prosthesis to span the entire aneurysm preventing pressure from acting on the damaged area, and to prevent leakage through any rupture of the aneurysm. In order for the prosthesis to span the aneurysm properly, the prosthesis should be accurately positioned.

The radial orientation of the prosthesis is also important to prevent twists in the prosthesis. This is especially important when the prosthesis is a bifurcated graft. Each leg of the bifurcated graft should be aligned with its intended vasculature branch, or the body lumen may become distended and the lumen of the graft may be distorted and even closed completely. If the bifurcated graft is assembled in situ, it may be impossible to deploy a leg of the graft into a misaligned port of the graft. Recapture or repositioning of an expanded prosthesis can be problematic, therefore it is very important to correctly align the prosthesis in the vasculature system.

Previous attempts have used radiopaque markers attached to the endovascular implant to facilitate positioning of endovascular prosthesis inside corporeal vessels. However, previous attempts could not readily identify all twists in the implant. Further, with the previous attempts, it could be difficult to orient a portion of the implant because the radiopaque markers had a low contrast and the markers would change shape when viewed under fluoroscopy which projects a two-dimensional image of a three-dimensional prosthesis.

For these reasons, it would be desirable to have an endovascular prosthesis with high contrast imaging markers that are able to detect the position and orientation of the prosthesis using a two-dimensional screen for viewing.

SUMMARY OF THE INVENTION

Briefly, and in general terms, the present invention is directed at an endovascular prosthesis having imagable markers disposed on a wall of the prosthesis in a pattern that will help determine the orientation and position of the prosthesis inside a vessel. The pattern of markers may be placed on any type of endovascular prosthesis, such as a tubular, tapered, flared, bifurcated or modular graft.

In one embodiment, a device for repairing a corporeal vessel includes a graft having a wall defining a lumen and a plurality of radiopaque markers disposed on the wall of the graft. Each radiopaque marker appears generally identical under fluoroscopy regardless of the grafts orientation inside the corporeal vessel. A first set of radiopaque markers is disposed on an anterior side of the graft and a second set of radiopaque markers is disposed on a posterior side of the graft. The first and second sets of radiopaque markers are disposed along a line parallel to a longitudinal line of the graft, wherein the first and second sets of radiopaque markers appear to form a single line under fluoroscopy when the anterior and posterior sides of the graft are aligned in the internal lumen. When the markers do not form a single straight line, it indicates that the graft is in a twisted or rotated position.

In another embodiment, the endovascular prosthesis includes a graft having a wall defining a lumen and a plurality of radiopaque markers disposed on the wall of the graft in an asymmetric pattern. Each radiopaque marker appears generally identical under fluoroscopy regardless of the grafts orientation inside the corporeal vessel. The asymmetric pattern of radiopaque markers includes a group of markers having at least a first, a second, and a third marker disposed on the wall of the graft along a line that is perpendicular to the longitudinal axis of the graft. The second marker located between the first and the third marker is positioned closer to the first marker than the third marker. A plurality of these groups of markers are disposed along the longitudinal axis of the graft, with each group of markers aligned with one another. This asymmetric pattern allows the distinction of whether the marker group is on the front or back side of the graft, depending on which side on which the first and second marker are placed. Also, the orientation of the marker groups allows the detection of twists or rotations in the graft.

The present invention is particularly useful in conjunction with a graft that is unsupported along a substantial portion of its length, because this type of graft is more susceptible to twists. However, previous grafts used have been supported all along their length, which eliminates the concern of the graft becoming twisted.

The above embodiments of the present invention may be used with any type of endovascular prosthesis, including a tubular graft, a tapered graft, a bifurcated graft, and a modular graft. Moreover, the present invention can be incorporated into the design of any medical device where it is important to know the placement and orientation of the device in vasculature.

These and other advantages of the invention will become more apparent from the following detailed description of the preferred embodiments. When taken in conjunction with the accompanying exemplary drawings the person of skill in the art will appreciate that various embodiments incorporate the present invention.

BRIEF DESCRIPTION OF THE DRAWINGS

FIG. 7 is a side elevational view of a crimped tubular graft leg having an inferior end with a larger diameter than a superior end;

FIG. 8 is a side elevational view of a crimped tubular graft leg having an inferior end with a smaller diameter than a superior end;

DETAILED DESCRIPTION OF THE PREFERRED EMBODIMENTS

The present invention relates to the use of imagable bodies, such as radiopaque markers, on an endovascular device to detect the orientation and position of the endovascular device during an implantation procedure. Each imagable body of the present invention appears generally identical to the others under fluoroscopy, which aides in providing a high contrast between the markers and any radiopaque material associated with the endovascular device and lowers the cost of the device. These generally identical markers may be used with any endovascular device.

Figure 1:
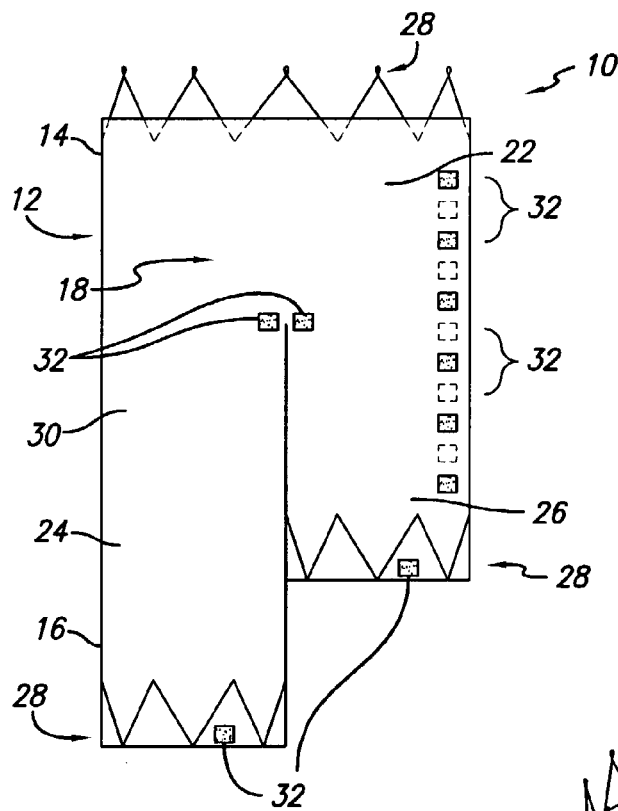
FIG. 1 is an elevational view of bifurcated graft having marker elements disposed along the contralateral stump side of the graft.
Figure 1A:
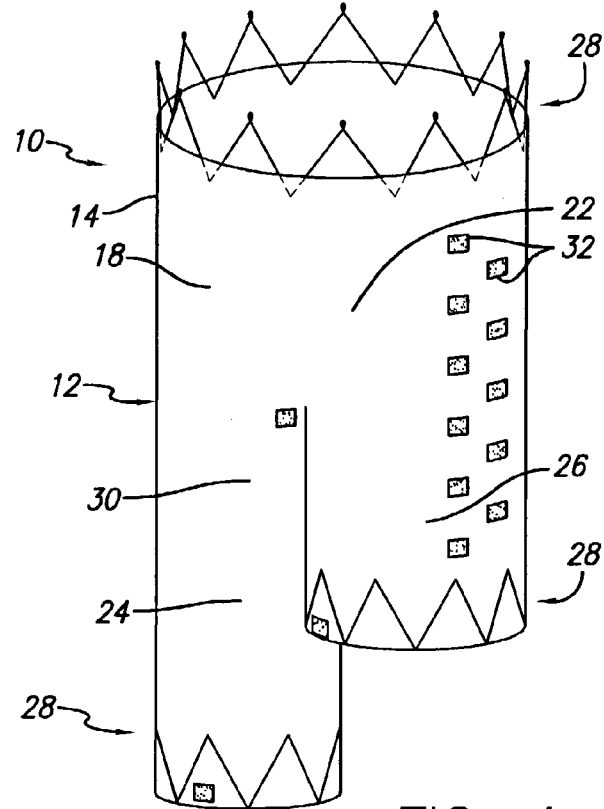
FIG. 1A is a partially rotated view of the bifurcated graft shown in FIG. 1.
Figure 2:
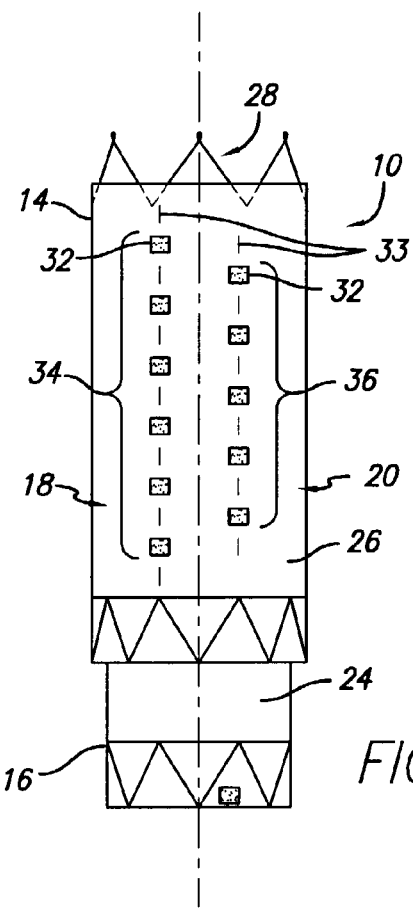
FIG. 2 is a side elevational view of the bifurcated graft shown in FIG. 1 with two sets of marker elements disposed along the contralateral stump side of the graft in a staggered configuration.
Figure 3:
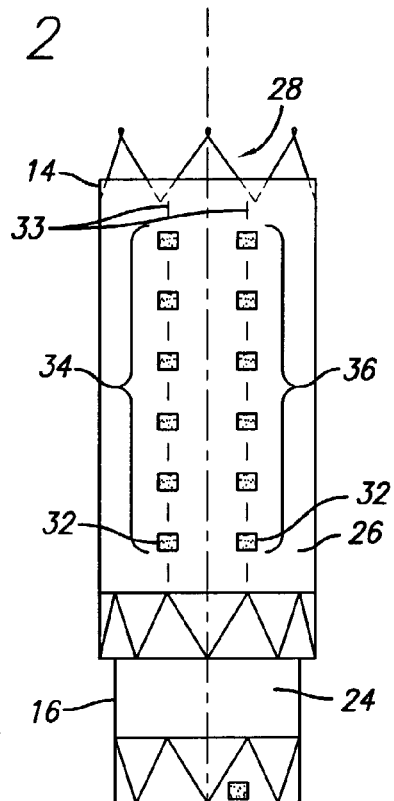
FIG. 3 is a side elevational view of a bifurcated graft having two sets of marker elements disposed along the contralateral stump side of the graft in a paired configuration.
Figure 4:
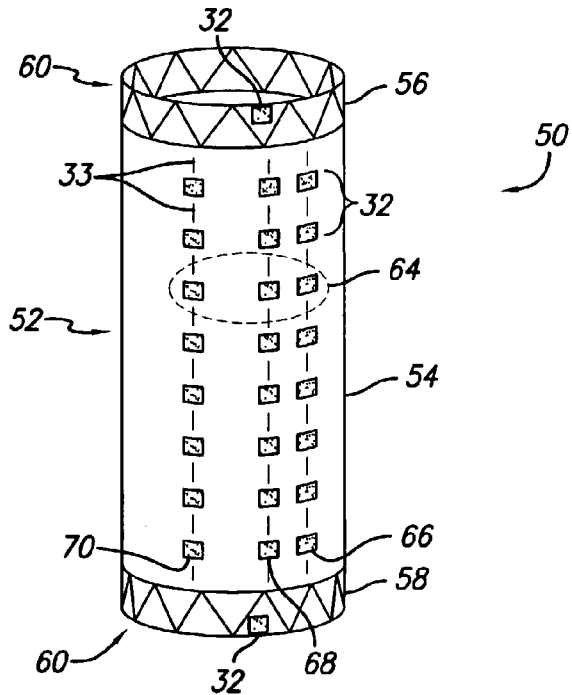
FIG. 4 is an elevational view of a tubular graft having marker elements disposed on the graft in an asymmetric pattern.

The figures show an endovascular prosthesis containing radiopaque markers for locating the prosthesis and for detecting any twisting of the prosthesis inside a corporeal vessel. FIGS. 1-3 depicts a bifurcated graft 10 having a graft body 12 with a superior end 14 and an inferior end 16. The graft body 12 also has an anterior side 18 and a posterior side 20. A main tubular member 22 with a longitudinal axis is located at the superior end 14 of the graft body, and the main tubular member bifurcates into an ipsilateral leg 24 and a contralateral stump 26 at the inferior end 16. The bifurcated graft 10 can be attached to the vessel lumen with attachment means 28 located at superior and inferior ends of the graft for a full length graft. There are several attachment means known in the art that may be used in conjunction with the graft described in this application. For shorter grafts, attachment means 28 at either or both inferior ends hold the graft open and limbs such as shown in FIG. 4 are added to the graft. A wall 30 defining a lumen is disposed over the main tubular member and the ipsilateral and contralateral legs.

Still referring to FIGS. 1-3, the bifurcated modular graft 10 includes a plurality of radiopaque markers 32 disposed on the wall 30 along the contralateral stump 26. In another embodiment, the markers 32 may be disposed along the ipsilateral leg instead of the contralateral stump. One embodiment depicted in FIG. 1 disposes two markers 32 above the bifurcation, and one marker disposed at the inferior end 16 of each leg 24 and 26. These markers allow a physician to view under fluoroscopy the location of the bifurcations and the ends of the graft. A radiopaque marker may also be disposed on the superior end of the graft, however the radiopacity of the attachment means should be sufficient to locate the superior end of the graft under fluoroscopy. It should be understood that the number of markers disposed on the graft may be altered without departing from the present invention.

Each of the markers 32 appears generally identical under fluoroscopy regardless of the orientation of the graft inside the corporeal vessel. The radiopaque markers 32 used in this embodiment are all identical coils made of a suitable material such as platinum tungsten alloy wire of a suitable diameter such as 0.004 inches (0.102 mm) which is wound into a spring coil having a diameter of 0.04 inches (1.02 mm). The length of the marker coils used on a graft are kept short, such that when viewed under fluoroscopy, the coiled markers each appear as a dot, regardless of the orientation of the graft. Attaching the coiled markers to the wall of the graft can be done in a number of ways known in the art, however in this embodiment the marker coils are sutured to the wall 30 of the graft by sutures 33.

In the embodiment shown in FIGS. 1-3, there is a first set of radiopaque markers 34 disposed on the anterior side 18 of the graft body 12 in a line parallel to the longitudinal axis of the main tubular member 22, and the first set of radiopaque markers 34 is positioned along the main tubular member and down the contralateral stump 26. A second set of radiopaque markers 36 is disposed on the posterior side 20 of the graft body 12 in a line parallel to the longitudinal axis of the main tubular member 22 and parallel to the first set of radiopaque markers 34. The second set of radiopaque markers is also positioned along the main tubular member and down the contralateral leg. It is preferred that the individual markers in each of the first and second sets 34 and 36 are each spaced approximately 5 mm to 8 mm apart from adjacent markers in the same set. It is also preferred that each set or row of radiopaque markers 34 and 36 is disposed in a line 5 mm from an anterior/posterior (A/P) line of the graft. It should be noted however that the distance between adjacent markers may be any distance apart, and that the sets or rows of radiopaque markers may be any equal distance from the anterior/posterior line of the graft.

As shown in FIGS. 1-2, the first and second set of radiopaque markers 34 and 36 are staggered (or in a zig-zag pattern) with respect to one another. The two lines of markers will form a single line under fluoroscopy when the graft is aligned anteriorly/posteriorly (as shown in FIG. 1), indicating that the graft is untwisted in the corporeal lumen. In another embodiment shown in FIG. 3, the second set of radiopaque markers 36 overlaps the first set of markers when viewed under fluoroscopy, indicating that the graft is aligned anteriorly/posteriorly in the corporeal lumen. This will be referred to as a paired pattern with markers from the first set of radiopaque markers "pairing up" with markers of the second set of radiopaque markers. With either of the two embodiment shown in FIGS. 1-3, if the graft is rotated out of position inside the corporeal lumen, or the graft is twisted, there will be two visible lines under fluoroscopy. Also, in both of these embodiments, with staggered or paired, the physician could also determine that a graft was angled from top to bottom. For example, in the paired configuration, the markers would start to appear staggered if the graft (and vessel) was tilted anteriorly or posteriorly.

In the staggered configuration, the markers would start to appear paired if the graft (and vessel) were tilted anteriorly or posteriorly. Knowing the tilting of the graft may aid during cannulation of the stump, in preparation for insertion of the limb graft.

Figure 9:
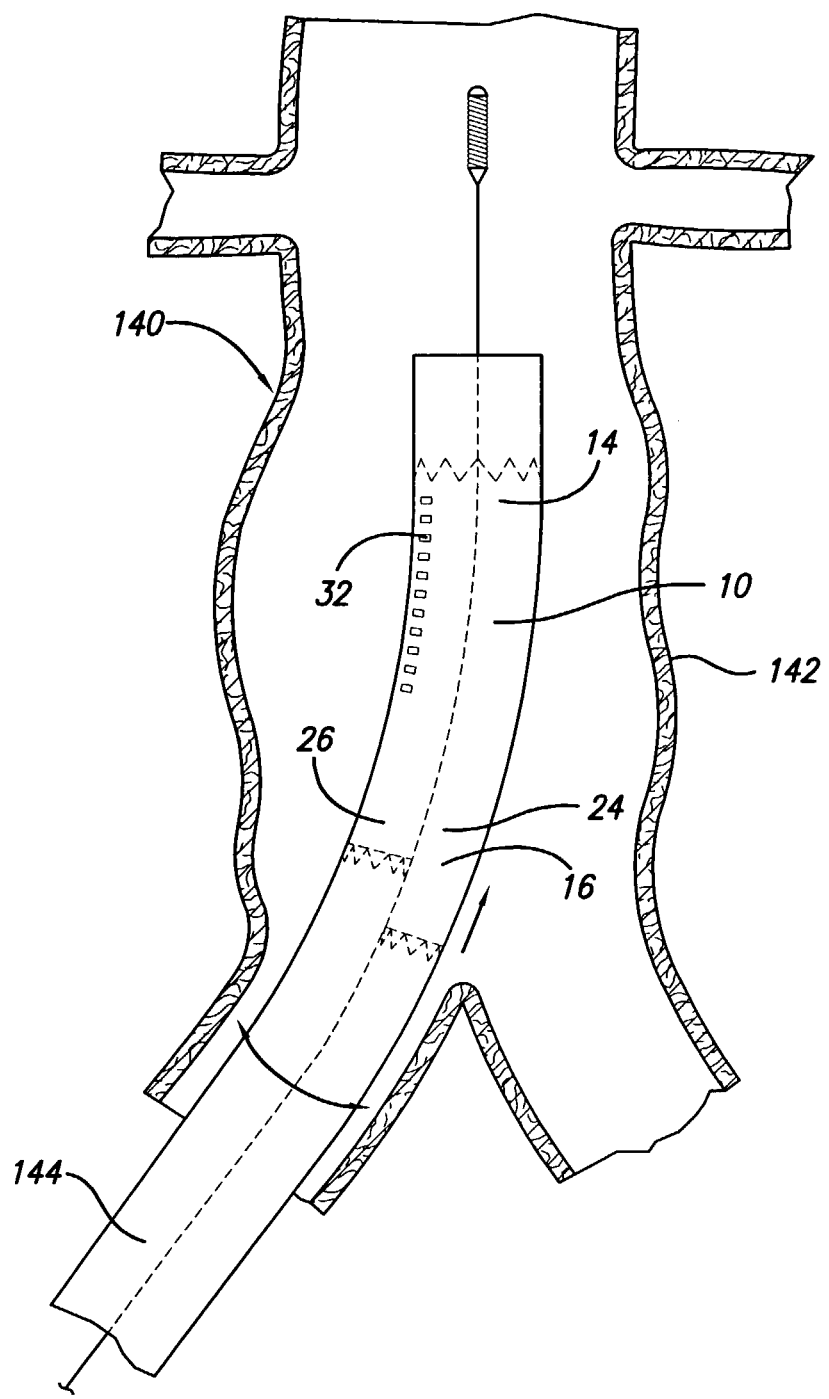
FIG. 9 is a cross sectional view of a bifurcation of the abdominal aortic artery during the insertion of a bifurcated graft, where the contralateral leg of the graft is on the wrong side of the aneurysm.
Figure 10:
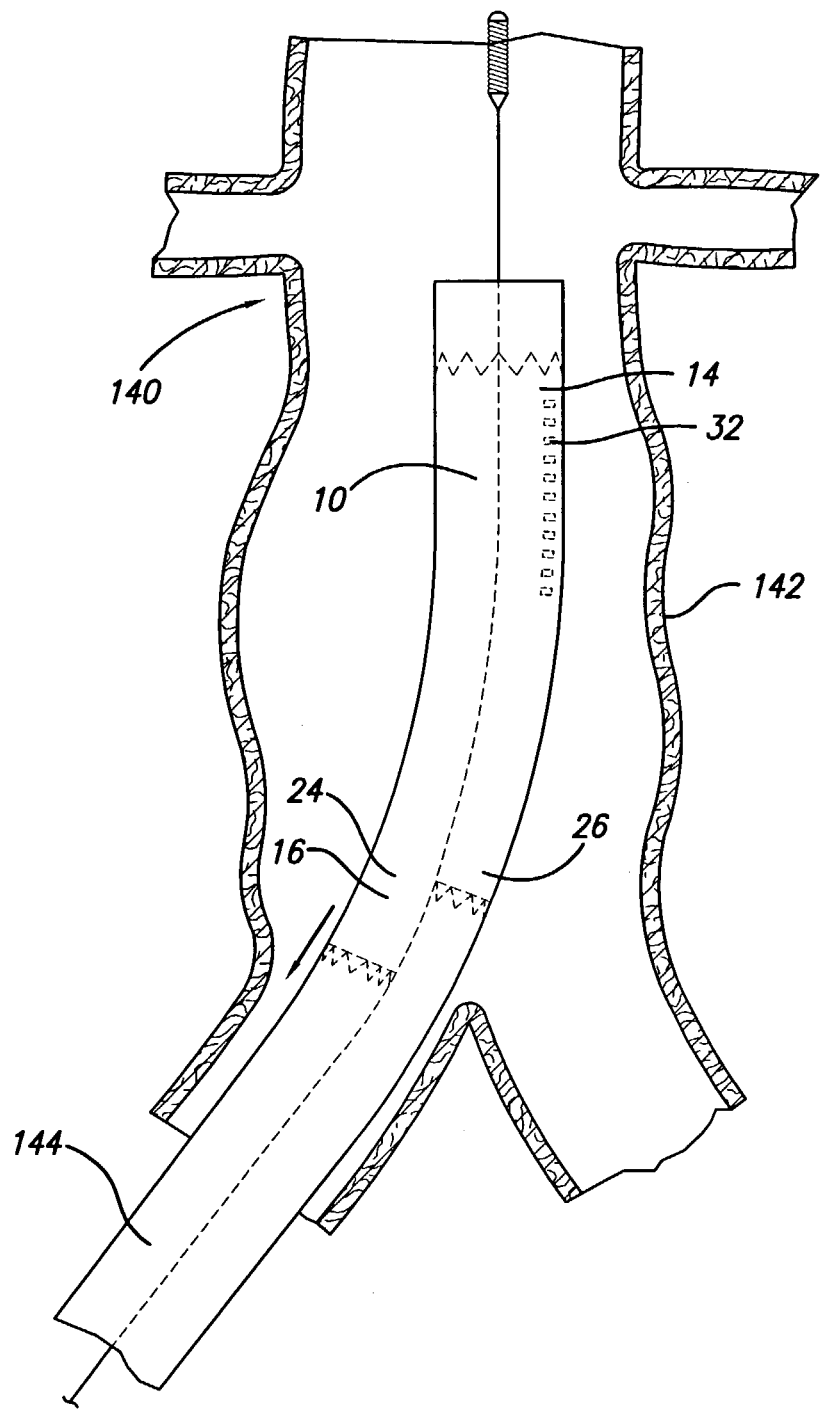
FIG. 10 is a cross sectional view where the bifurcated graft of FIG. 9 has been rotated, placing the contralateral leg on the contra, or correct side of the aneurysm.
Figure 11:
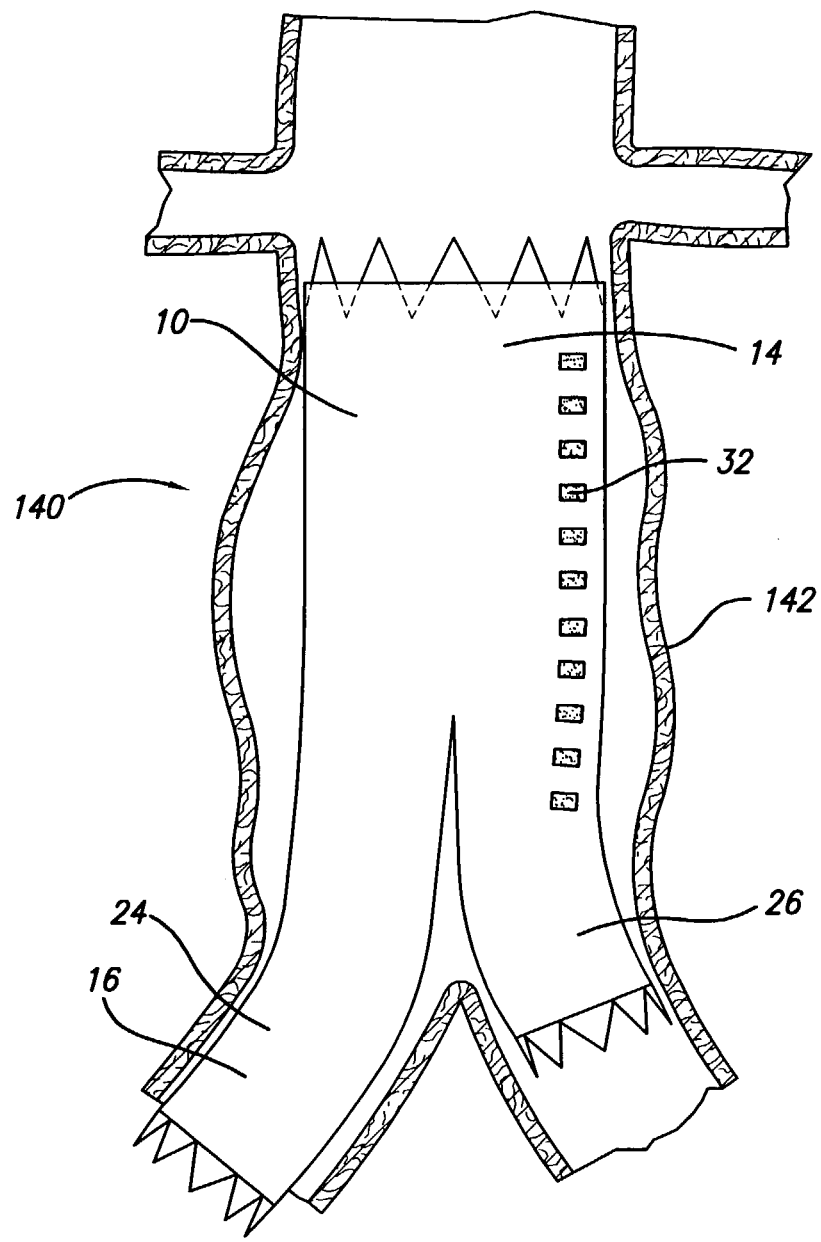
FIG. 11 is a cross sectional view where the bifurcated graft of FIGS. 9 and 10 has been released from the sheath at the abdominal aortic aneurysm.

These embodiments also let a user know when the contralateral stump 26 or the ipsilateral leg 24 is on the wrong side of the aneurysm, because the user will initially know which side of the graft the markers are located. Referring now to FIGS. 9-11, a procedure to deploy a bifurcated graft 10 in a corporeal lumen 140 having an aneurysm 142, is shown. FIG. 9 shows the bifurcated graft 10 loaded into a delivery catheter 144, and positioned at the aneurysm inside the corporeal lumen. While the graft is contracted inside the delivery catheter, a physician will be able to view the markers under fluoroscopy to determine the positioning of the graft, and whether the contralateral leg of the bifurcated graft is on the correct side of the aneurysm. In FIG. 9, the markers 32 indicate that the contralateral leg is on the wrong side of the aneurysm. In this situation, the physician would torque the catheter until the markers indicate that the contra leg is on the correct side of the aneurysm as shown in FIG. 10. Once it is determined that the graft is aligned correctly, that the contralateral leg is on the correct side of the aneurysm, the bifurcated graft can be deployed from the catheter and into the corporeal lumen. The physician will also be able to view the rotational orientation of the bifurcated graft 10 under fluoroscopy and can properly align the bifurcated graft in an anterior/posterior orientation inside the corporeal lumen. As shown in FIGS. 10 and 11, the marker 32 form a single line under fluoroscopy indicating that the graft is properly aligned anteriorly/posteriorly. In addition, FIG. 11 shows the bifurcated graft expanded in position at the aneurysm.

The above embodiments shown in FIGS. 1-3 improve visualization of the main body or aortic portion of the modular implants. It is important that the implant is deployed anteriorly/posteriorly so that the contralateral stump opens on the contra side of the aneurysm for ease of cannulation through the contra iliac. Although the above embodiments disclose the use of radiopaque markers on a modular graft, these marker patterns may be used on any other type of graft as well, such as a tubular graft or a bifurcated graft with two legs of length sufficient to reach past the aortic bifurcation (a unibody graft).

Referring now to FIG. 4, a tubular graft 50 (which can be the limb of a modular graft) is shown containing radiopaque markers for locating the graft and for detecting any twisting of the graft inside a corporeal vessel. The tubular graft 50 includes a graft body 52 having a tubular member 54 formed along a longitudinal axis with a superior end 56 and an inferior end 58. Attachment means 60 are also located at the superior and inferior ends of the tubular member 54 for attaching the graft to the vessel and/or to another graft. There are several types of attachment means known in the art that may be used in conjunction with the grafts described in this application.

There are a plurality of radiopaque markers 32 disposed on the graft body 52, with each marker having the same size and appearing identical under fluoroscopy regardless of the grafts orientation inside the corporeal vessel. The radiopaque markers 32 discussed here have the same characteristics and properties as the radiopaque markers 32 discussed above in the previous embodiments. Radiopaque markers 32 may also vary in size depending on the size of the tubular graft 50 and may be attached to the graft wall by any means including suturing.

As shown in FIG. 4, the radiopaque markers 32 are disposed on the graft body 52 in an asymmetric pattern. The asymmetric pattern of this embodiment includes a group of radiopaque markers 64 having at least a first 66, a second 68, and a third 70 radiopaque marker disposed on the graft body 52 along a line that is perpendicular to the longitudinal axis. The second marker 68 is located between the first 66 and the third 70 marker and is closer to the first marker than the third marker. This arrangement provides a relatively larger gap between the second and third marker than the gap between the first and second marker. It is possible for the second marker 68 to be closer to the third marker 70 than the first marker 66, which still provides an asymmetric pattern. This embodiment also includes a plurality of groups of radiopaque markers disposed along the longitudinal axis of the graft body, with each group of markers aligned with the adjacent group of markers. This asymmetric pattern distinguishes between the marker group being on the front or back side of the graft, depending on which side the first and second markers are on. Also, the orientation of the marker groups allows the detection of twists or rotations in the graft.

Radiopaque markers 32 may also be placed at the superior 56 and inferior 58 ends of the graft 50 to indicate under fluoroscopy where the ends are located in the corporeal lumen. The embodiment shown in FIG. 4 has one marker 32 disposed at the superior end 56, and one marker disposed at the inferior end 58. However, the number of markers disposed at the ends may vary.

Figure 4A:
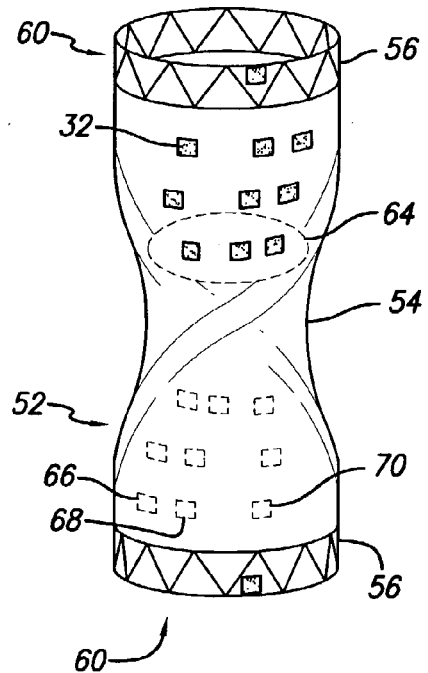
FIG. 4A is an elevational view of the tubular graft shown in FIG. 4 that is twisted 180° around.

The asymmetrical pattern of the radiopaque markers 32 shows when the implant is twisted because the spacing of the marker further away, in this embodiment the third marker 70, will change from one side to the other. Even if the implant is twisted 180° from the superior end 56 to the inferior end 58 as shown in FIG. 4a, the twist will still be detectable, because the spacing between the second and third markers at the superior end 56 will be on the left-hand side indicating that the markers are on the anterior or front side of the implant, while the spacing between the second and third markers at the inferior end 58 will be on the right-hand side indicating that the markers are on the posterior or back side of the implant. With the use of symmetrical patterns of markers on the implant, it can be difficult to determine when the implant is twisted all the way around (180°) or if the implant is only twisted one way and then back the other direction. However, the asymmetrical marker group pattern is able to detect these types of twists when viewing the three-dimensional implant in two-dimensions.

It should be understood that an important aspect of this embodiment is that the markers are disposed in an asymmetrical pattern. The pattern does not have to be as described above, and the markers can be in any asymmetrical pattern. Further, this embodiment can be used on any tubular object such as the legs of a bifurcated graft.

Figures 12, 13:
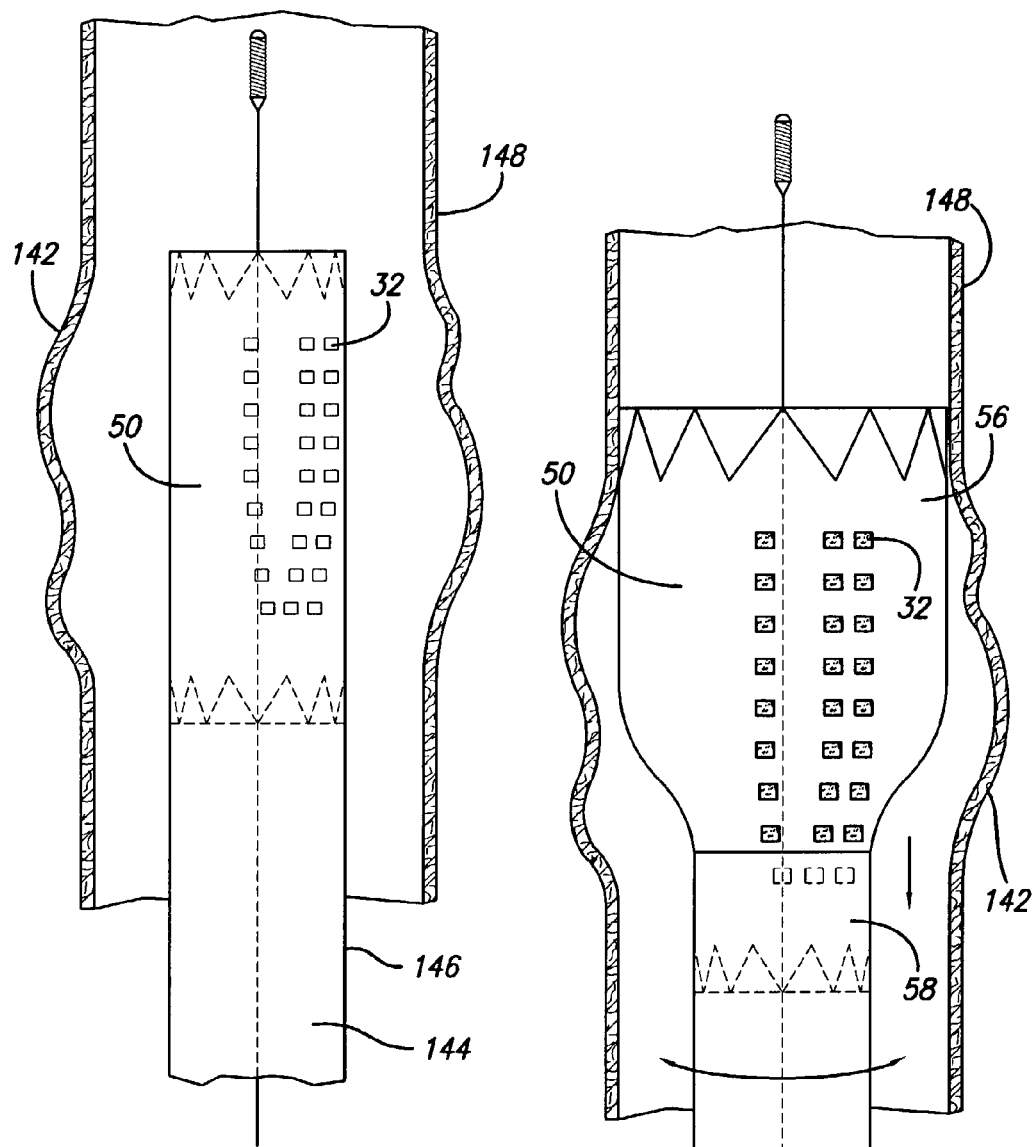
FIG. 12 is a cross sectional view of an aneurysm of a corporeal vessel during the insertion of a tubular graft, where markers on the graft indicate that the graft is twisted.
FIG. 13 is a cross sectional view where the superior end of the graft of FIG. 12 has been released from the sheath, while the inferior end of the graft remains inside the sheath.
Figure 14:
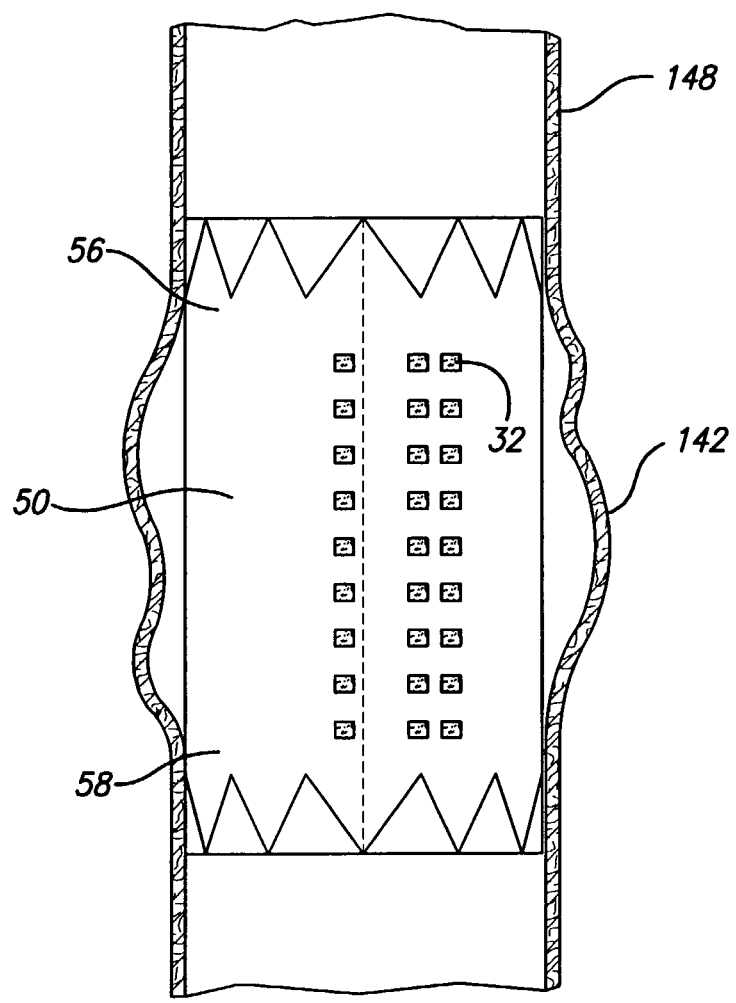
FIG. 14 is a cross sectional view where the graft of FIGS. 12-13 is released from the sheath and the graft is untwisted.

During the procedure for positioning a graft 50 in a corporeal lumen, which is shown in FIGS. 12-14, the graft would first be loaded into a guiding catheter 144 and covered by a sheath 146. The graft and at least a portion of the sheath would then be introduced into a vessel 148, to position the graft at a target location such as an aneurysm 142 inside the vessel. The sheath 146 can then be pulled back from a portion of the graft, as shown in FIG. 13 exposing at least the superior end 56 of the graft, and leaving at least the inferior end 58 of the graft covered by the sheath. Under fluoroscopy, a physician will be able to view the markers 32 on the graft and detect any twists in the graft, such as the slight twist shown in FIG. 13. If a twist is found in the graft, the catheter is used to untwist the graft before removing the sheath completely from the graft and releasing the graft into the corporeal lumen as depicted in FIG. 14.

Figure 5:
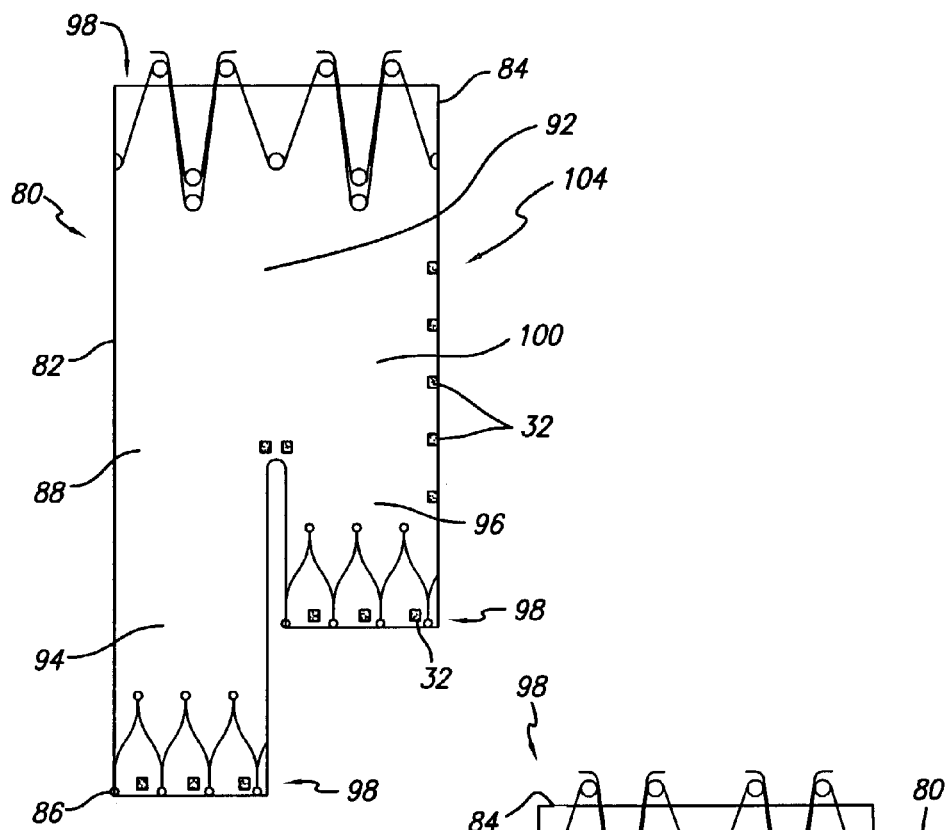
FIG. 5 is an elevational view of a bifurcated graft having marker elements disposed along the contralateral stump side of the graft.
Figure 6:
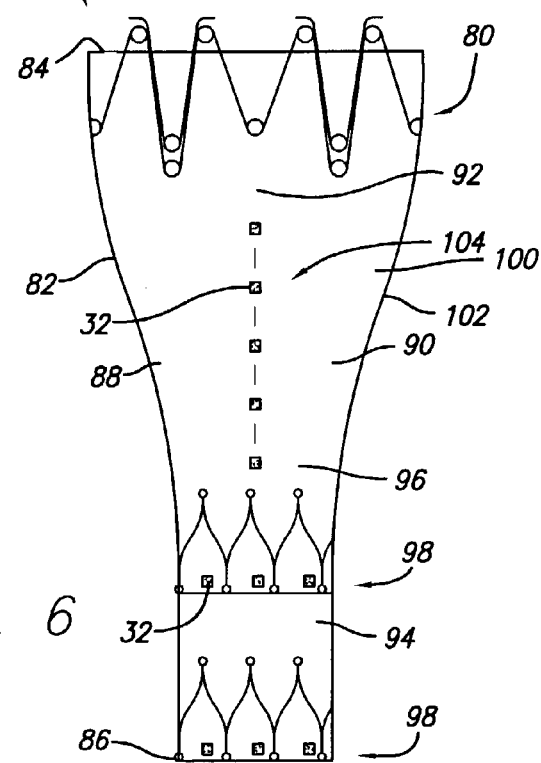
FIG. 6 is a side elevational view of the bifurcated graft shown in FIG. 5.

Another embodiment is shown in FIGS. 5 and 6, where a main body implant is a bifurcated graft 80 having a graft body 82 with a superior end 84 and an inferior end 86. The graft body 82 also has an anterior side 88 and a posterior side 90. A main tubular member 92 with a longitudinal axis is located at the superior end 84 of the graft body, and the main tubular member bifurcates into an ipsilateral leg 94 and a contralateral stump 96 at the inferior end 86. The bifurcated graft 80 can be attached to the vessel lumen with attachment means 98 located at superior and inferior ends of the graft for a full length graft. For shorter grafts, attachment means 98 at either or both the inferior ends hold the graft open and limbs such as those shown in FIGS. 7 and 8 are added to the graft. A wall 100 defining a lumen is disposed over the main tubular member and the ipsilateral and contralateral legs. In the side elevational view shown in FIG. 6, it can be seen that the bifurcated graft 80 includes a taper 102 between the main tubular member 92 and the ipsilateral and contralateral legs 94 and 96. The degree of the taper may vary depending on the diameter of the main tubular member at the superior end 84 and the diameter at the inferior ends 86 of the legs 94 and 96.

Still referring to FIGS. 5 and 6, the bifurcated graft 80 includes a plurality of radiopaque markers 32 (identical to those previously described) disposed on the wall 100 along the anterior/posterior line (A/P line) of the contralateral stump 96. In another embodiment, the markers 32 may be disposed along the ipsilateral leg instead of the contralateral stump. This embodiment also includes two markers 32 disposed above the bifurcation, and six markers disposed at the inferior end 86 of each leg 94 and 96. These markers allow a physician to view under fluoroscopy the location of the bifurcation and the ends of the graft. A radiopaque marker may also be disposed on the superior end of the graft, however the radiopacity of the attachment means should be sufficient to locate the superior end of the graft under fluoroscopy. It should be understood that the size and number of markers disposed on the graft may be altered without departing from the present invention.

In the embodiment shown in FIGS. 5 and 6, there is a set of radiopaque markers 104 disposed along the A/P line on the contralateral leg 96 the graft body 82 in a line parallel to the longitudinal axis of the main tubular member 92. The figures show five markers 32 included in the set of markers 104, however the number of markers in the set can vary depending on the length of the graft. The individual markers in the set of markers 104 are each spaced approximately 5 mm to 8 mm apart from adjacent markers in the same set. It is preferred that the markers are about 8 mm apart, center to center of the adjacent markers. In a preferred embodiment, the first marker nearest the superior end 84 of the graft is located about 17 mm-19 mm from the superior end of the graft. The marker nearest the inferior end 86 is located about 2 mm-3 mm from the edge of the attachment means 98 at the inferior end of the contralateral stump 96.

A crimped tubular leg graft, generally designated 110, is shown in FIGS. 7 and 8, and may be used in connection with the bifurcated graft 80 shown in FIGS. 5 and 6. The crimped tubular legs 110 of FIGS. 7 and 8 each have a tubular body 112 with superior 114 and inferior 116 ends. There is a superior cylinder 118 located at the superior end 114 of the tubular leg 110 with a specific diameter including a lock stent 120 having hooks 121 to secure the tubular leg to the main limb implant. The tubular leg 110 also includes a crimped cylinder 122 with a plurality of crimps 124 along a longitudinal axis, and an uncrimped flared cylinder 126. At the inferior end 116 of the tubular leg 110 is an inferior cylinder 128 with a specific diameter including a limb stent 130 and hooks 134 for securing the tubular leg to the corporeal lumen. The diameter of the inferior cylinder 128 can vary in size depending on the size of the vessel where it will be located.

Referring to FIG. 7, a tubular leg 110 is shown where the diameter of the inferior cylinder 128 is larger than the diameter of the superior cylinder 118. The tubular leg 110 in FIG. 7 has a pattern from the superior end to the inferior end starting with the superior cylinder 118 with the lock stent 120, followed by the crimped cylinder 122, which leads to the uncrimped flared cylinder 126 that flares out to the larger diameter of the inferior cylinder 128 with the limb stent 130. The diameter of the crimped cylinder is essentially equal to the diameter of the superior cylinder.

Referring now to FIG. 8, the tubular leg 110 has an inferior cylinder 128 with a diameter smaller than the diameter of the superior cylinder 114. The tubular leg 110 in FIG. 8 has a pattern from the superior end to the inferior end, starting with the superior cylinder 118 with the lock stent 120, followed by the uncrimped flared cylinder 126 that flares out toward the superior end and tapers down to the smaller diameter of the crimped cylinder 122 which follows, and leads into the inferior cylinder 128 with the limb stent 130. The diameter of the crimped cylinder is essentially equal to the diameter of the inferior cylinder.

The lock stent 120 shown in FIGS. 7 and 8 is located internal to the graft material and is self-expanding with a series of caudal hooks or barbs 121 that extend through relief holes 132 that are spaced around the circumference of the superior cylinder 118 to correspond to the hooks or barbs 121. The lock stent 120 is attached to the superior cylinder 118 using sutures such that the hooks or barbs 121 protrude through the holes 132 when the tubular leg 110 is compressed for delivery, thereby preventing the compressed hook or barb 121 from tearing the graft material. The lock stent 120 is designed to be attached to an inferior end 86 of the bifurcated graft 80 inside either the ipsilateral or contralateral leg 94 or 96. It is preferred that there are five hooks or barbs 121 equally spaced around the lock stent 120, however the number of hooks can vary.

The limb stent 130 is also self-expanding and is designed to be attached to the vessel wall to anchor the inferior end 116 of the tubular leg 110. The limb stent 130 can be located internal to the graft material of the inferior cylinder 128 as shown in FIG. 7, or it may be located on the exterior of the inferior cylinder as shown in FIG. 8, however it is preferred for the limb stent to be on the interior (internal to graft material) to aid in the apposition of graft material to wall of vessel for purposes of sealing the anastamosis. The limb stent 130 is shown to have three hooks 134 extending beyond the inferior end 116 of the tubular leg, however any number of hooks may be used, and they may also be located inside the inferior cylinder 128 and extending through relief holes.

Note that the hooks or barbs 121 at the superior end 114 are angled in the inferior direction, which is the direction of blood flow in the vessel. This angling helps to ensure better attachment of the tubular leg 110 to the main implant 80. The barbs on the inferior end 116 of the tubular leg point opposite to the blood flow. When the tubular leg 110 is compressed for delivery, the hooks or barbs 121 and 134 of the stents 120 and 130 are also at least partially compressed. In a preferred embodiment, the relief holes 132 are pre-punctured using a hot pin to melt the graft material 83, or ultrasonically punched, allowing the five stent hooks 121 to protrude through the graft material 83 when the limb component 80 is compressed for delivery. When the limb component 80 is deployed within the ipsilateral or contralateral limb 94 or 96 of a main implant 80, the stent 120 will expand, thereby causing the hooks 121 to penetrate the graft material of the main body component 30, forming a seal and anchoring the limb component 80 within the main body component 30. A balloon can also be used to set the hooks. A "tug" in the distal direction can also set the hooks.

Radiopaque markers 32 are also disposed on the surfaces of the tubular legs 110 as shown in FIGS. 7 and 8. In this embodiment, a pair of markers 32 are aligned longitudinally along the tubular leg and are attached to the crimped cylinder and the uncrimped flared cylinder. The alignment of two markers 32 along the tubular graft is enough to show twists when the graft is viewed under fluoroscopy. An asymmetric pattern of markers may also be disposed along the tubular graft. The embodiments shown in the figures also include radiopaque markers attached to the superior end 114 of the leg 110 and the inferior end 116 of the leg to indicate under fluoroscopy where the ends of the tubular leg are located inside the vessel. The pair of markers 32 aligned on the tubular leg are spaced two crimps from each other, and about 7 mm-9 mm from the inferior edge of the lock stent 120 to the first pair of radiopaque markers. The pair of markers disposed on the uncrimped flared cylinder 126 nearest to the crimped cylinder 122 are spaced about 11 mm-13 mm from the nearest pair of markers located on the crimped cylinder. Although the figures show nine pairs of markers 32 aligned on the tubular leg, the number may vary depending on the length of the tubular graft The size of the markers may vary and the location of the pairs of markers may also vary on the tubular legs.

The above embodiments are used by visualizing the marker images under fluoroscopy during deployment of the implant. An operator can observe the relative position and/or movement of the marker images during the procedure to help ensure proper deployment of the implant. The marker patterns can also be viewed post procedure on a still image to see the orientation of the implant in the vessel.

It will be apparent from the foregoing that, while particular forms of the invention have been illustrated and described, various modifications can be made without departing from the spirit and scope of the invention.

Accordingly, it is not intended that the invention be limited, except as by the appended claims.

What is claimed is:

1. A device for repairing a corporeal vessel, comprising:
    a graft having a wall defining a lumen;
    and a plurality of imagable markers, each having a substantially same size and shape, disposed on the graft in first and second sets, each marker of the first set of markers defining a first layout configuration and each marker of the second set of markers defining a second layout configuration circumferentially spaced from the first layout configuration,
    wherein a relative relationship between the first and second sets of markers indicates the rotational orientation of the graft inside the corporeal vessel,
    wherein the first set of markers is disposed on an anterior side of the graft and the second set of markers is disposed on a posterior side of the graft,
    wherein the first and second sets of markers are disposed along a first and a second line respectively, the first and second lines parallel to a longitudinal line of the graft, and
    wherein all of the markers of the first and second sets of markers form a single line of non-overlapping markers when the anterior and posterior sides of the graft are aligned in an internal lumen of the corporeal vessel.

2. The device of claim 1, wherein the graft has a main tubular member that bifurcates into an ipsilateral leg and a contralateral leg, and at least one of the sets of markers are disposed on at least one of the main tubular member, ipsilateral and contralateral leg.

3. The device of claim 1, wherein the first set of markers are configured such that the markers extend along the first line and have axial first spaces therebetween and wherein the second set of markers are configured such that the markers extend along the second line parallel to the first line and are spaced axially such that each marker of the second set axially aligns with a first space of the first set of markers.

4. A graft containing radiopaque markers for locating the graft and for detecting any twisting of the graft inside a corporeal vessel, comprising:
    a graft body having a superior end and an inferior end, and an anterior side and a posterior side, the graft body having a main tubular member at the superior end along a longitudinal axis, the main tubular member bifurcates into an ipsilateral leg and a contralateral leg at the inferior end; and
    a plurality of imagable markers, each having the substantially same size and shape, disposed on at least one of the ipsilateral and contralateral legs in first and second sets, each marker of the first set of markers defining a first layout configuration and each marker of the second set of markers defining a second layout configuration circumferentially spaced from the first layout configuration,
    wherein a relative relationship between the first and second sets of markers indicates the rotational orientation of the graft inside the corporeal vessel,
    wherein the first set of markers is disposed on the anterior side of the graft body in a line parallel to the longitudinal axis of the main tubular member and positioned along the contralateral leg, and the second set of markers is disposed on the posterior side of the graft body in a line parallel to the longitudinal axis of the main tubular member and positioned along the contralateral leg, and
    wherein all of the markers of the first and second sets of markers form a single line of non-overlapping markers when the anterior and posterior sides of the graft are aligned in an internal lumen of the corporeal vessel.

5. The graft of claim 4, wherein the radiopaque markers are spring coils.

* * * * *